Figure 3A:
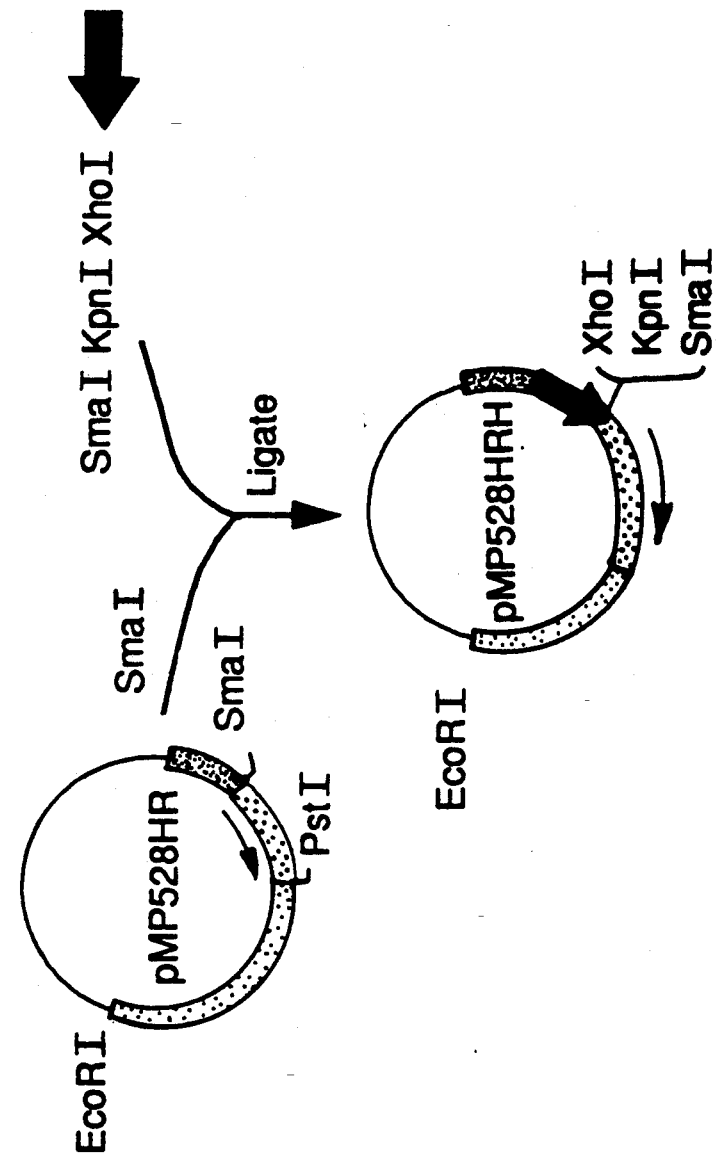

United States Patent [19]
Paoletti

[11] Patent Number: 5,155,020
[45] Date of Patent: Oct. 13, 1992

[54] RECOMBINANT POXVIRUS HOST RANGE SELECTION SYSTEM

[75] Inventor: Enzo Paoletti, Albany, N.Y.

[73] Assignee: Health Research Inc., Albany, N.Y.

[21] Appl. No.: 320,471

[22] Filed: Mar. 8, 1989

[51] Int. Cl.⁵ .................. C12P 21/02; C12N 15/64; C12N 15/86; C12N 15/00

[52] U.S. Cl. .................. 435/69.1; 435/172.3; 935/60; 935/79

[58] Field of Search .................. 435/172.3, 320.1, 69.1

[56] References Cited

FOREIGN PATENT DOCUMENTS

WO89/12103 12/1989 PCT Int'l Appl. .

OTHER PUBLICATIONS

Isle et al., Virology 112, 306–317 (1981).
Beck, E., Ludwig, G., Auerswald, E. A., Reiss, B., and H. Schaller, Gene 19, 327–336 (1982).
Boyle, D. B. and B. E. H. Coupar, Gene 65, 123–128 (1988).
Chakrabarti, S., Brechling, K., and B. Moss, Mol. Cell Biol. 5, 3403–3409 (1985).
Clewell, D. B., J. Bacteriol. 110, 667–676 (1972).
Clewell, D. B. and D. R. Helinski, Proc. Natl. Acad. Sci. USA 62, 1159–1166 (1969).
Drillien, R., Koehren, F., and A. Kirn, Virology 111, 488–499 (1981).
Drillien, R., Spehner, D., and A. Kirn, J. Virol. 28, 843–850 (1978).
Falkner, F. G. and B. Moss, J. Virol. 62, 1849–1854 (1988).
Fathi, Z., Sridhar, P., Pacha, R. F., and R. C. Condit, Virology 155, 97–105 (1986).
Fenner, F., and J. F. Sambrook, Virology 28, 600–609 (1966).
Franke, C. A., Rice, C. M. Strauss, J. H., and D. E. Hruby, Mol. Cell. Biol. 5, 1918–1924 (1985).
Gangemi, J. D., and D. G. Sharp, Virology 85, 262–270 (1978).
Gemmell, A., and F. Fenner, Virology 11, 219–235 (1960).
Gillard, S., Spehner, D., and R. Drillien, J. Virol. 53, 316–318 (1985).
Gillard, S., Spehner, D., Drillien, R., and A. Kirn, Proc. Natl. Acad. Sci. USA 83, 5573–5577 (1986).
Graham, F. L. and A. J. Van der Eb, Virology 54, 536–539 (1973).
Hruby, D. E., Lynn D. L. Condit, R., and J. R. Kates, J. Gen. Virol. 47, 485–488 (1980).
Kieny, M. P., Lathe, R., Drillien, R., Spehner, D., Skory, S., Schmitt, D., Wictor, T., Koprowski, H., and J. P. Lecocq, Nature (London) 312 163–166 (1984).
Lake, J. R., and P. D. Cooper, J. Gen. Virol. 48, 135–147 (1980).
Mackett, M., Smith, G. L. and B. Moss, Proc. Natl. Acad. Sci. USA 79, 7415–7419 (1982).
Mackett, M. and J. R. Arrand, EMBO J. 4, 3229–3235 (1985).
Mayr, A., Hochstein-Mintzel, V., and H. Stickl, Infection 3, 6–14 (1975).
McClain, M. E., Aust. J. exp. Biol. med. Sci. 43, 31–44 (1965).

(List continued on next page.)

*Primary Examiner*—Richard A. Schwartz
*Assistant Examiner*—S. L. Nolan
*Attorney, Agent, or Firm*—Curtis, Morris & Safford

[57] ABSTRACT

What is described is a selection system for the cloning and expression of open reading frames in poxviruses, particularly vaccinia virus. The selection system is based on a conditional lethal mutant (host range) of poxviruses. A deletion/recombinant mutant of the vaccinia virus was generated which is capable of plaquing on primary chick embryo fibroblasts and two monkey cell lines (BSC-40 or VERO) but is defective in replication in the human cell line MRC-5. Insertion of the host range gene into the deletion/recombinant restores the ability for growth on MCR-5 cells. A series of plasmids were constructed which allow for the rapid single-step cloning and expression of any open reading frame when recombined with the deletion/recombinant and scored for growth on MCR-5 cells.

10 Claims, 4 Drawing Sheets

OTHER PUBLICATIONS

Moyer, R. W. and C. T. Rothe, Virology 102, 119–132 (1980).

Nakano, E., Panicali, D., and E. Peoletti, Proc. Natl. Acad. Sci. USA 79, 1593–1596 (1982).

Panicali, D., Davis, S. W., Mercer, S. R. and E. Paoletti, J. Virol. 37, 1000–1010 (1981).

Panicali, D., and E. Paoleti, Proc. Natl. Acad. Sci. USA 79, 4927–4931 (1982).

Panicali, D., Grzelecki, A., and C. Hwang, Gene 47, 193–199 (1986).

Perkus, M. E. Panicali, D., Mercer, S., and E. Paoletti, Virol. 152, 285–297 (1986).

Perkus, M. E., Piccini, A., Lipinskas, B. R., and E. Paoletti, Science 229, 981–984 (1985).

Piccini, A., Perkus, M. E. and E. Paoletti, In: Methods in Enzymology, vol. 153, ed. Wu, R. and L. Grossman (Academic Press), pp. 545–563 (1987).

Rosel, J. L., Earl, P. L., Weir, J. P., and B. Moss, J. Virol. 60 436–449 (1986).

Shapira, S. K., Chou, J., Richaud, F. V., and M. J. Casadaban, Gene 25, 71–82 (1983).

Southern, P. H. and P. Berg, J. Mol. Appl. Genet. 1, 327–341 (1982).

Tagaya, I., Kitamura, T., and Y. Sano, Nature (London) 192, 381–382 (1961).

Wachsman, M., Aurelian, L., Smith, C. C., Lipinskas, B. R., Perkus, M. E., and E. Paoletti, J. Inf. Dis. 155, 1188–1197 (1987).

Wilson, E. M., W. M. Hodges and D. E. Hruby, Gene 49, 207–213 (1986).

Yuen, L., and B. Moss, Proc. Natl. Acad. Sci. USA 84, 6417–6421 (1987).

Kotwal, G. J. and B. Moss, Virology 167, 524–537 (1988).

Perkus et al., *Virology*, vol. 179, No. 1, pp. 276–286 (1990).

Lai et al., *Microbial Pathogenesis*, vol. 6, No. 3, pp. 219–226 (1989).

Goebel et al., *Virology*, vol. 179, No. 1, pp. 247–266 (1990).

Altenburger et al., *Archives of Virology*, vol. 105, pp. 15–27 (1989).

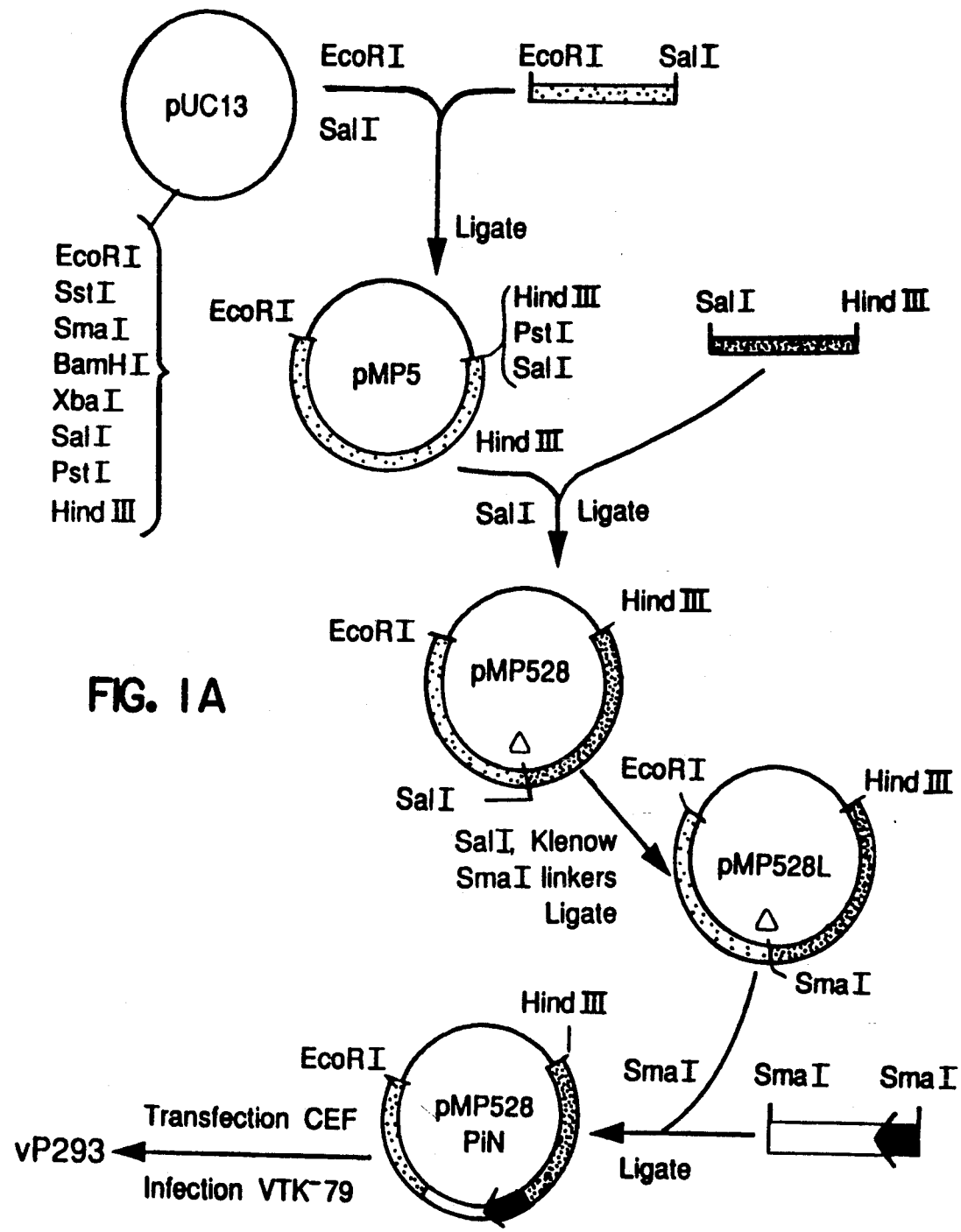
FIG. 1A
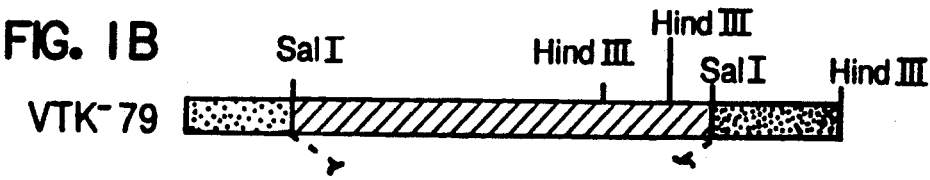
FIG. 1B VTK⁻79
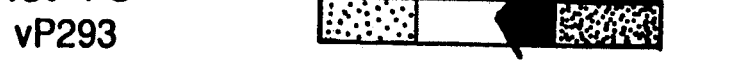
FIG. 1C vP293

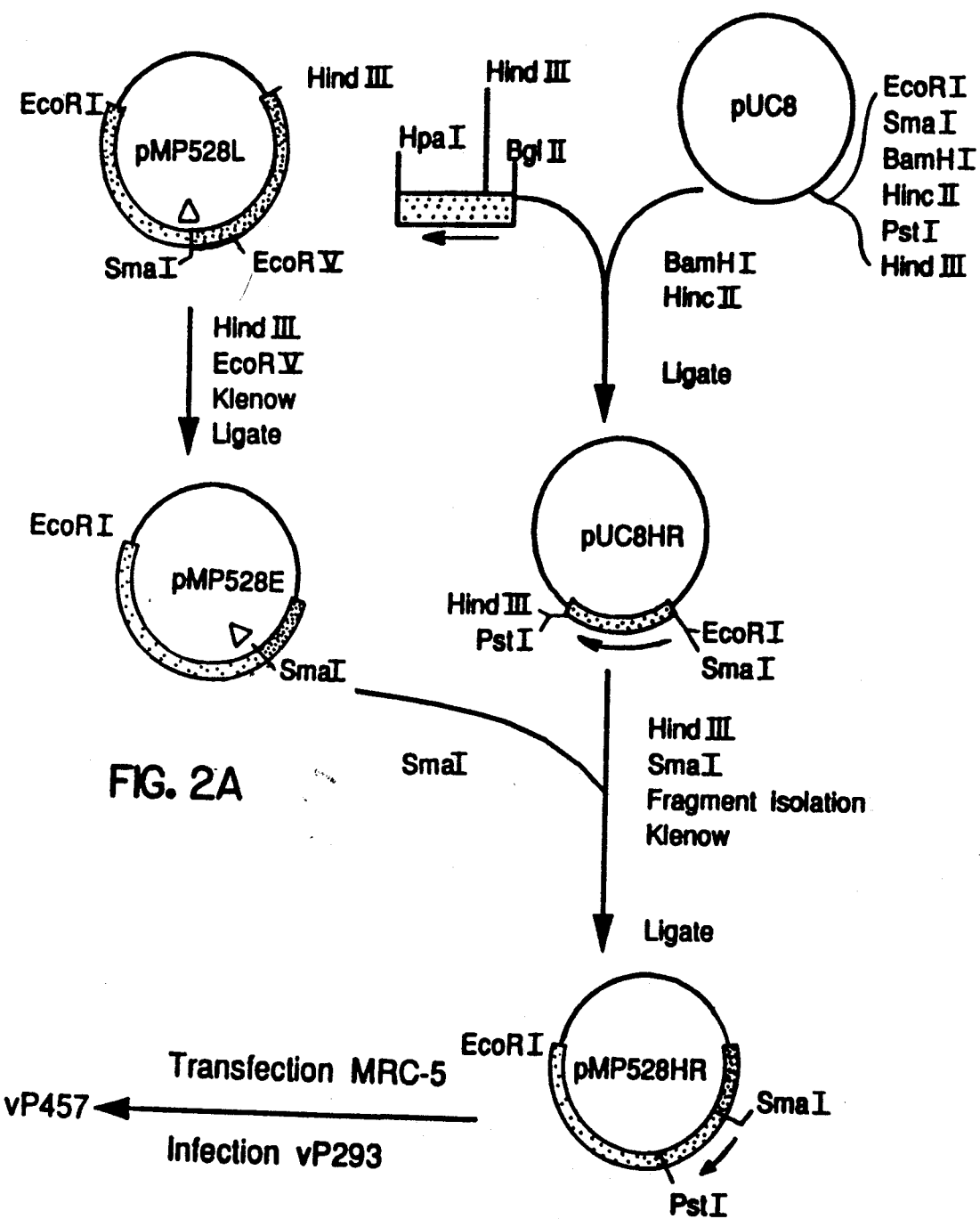

FIG. 3B TCTTTATTCTATACTTAAAAAGTGAAATAAATACAAAGGTTCTTGAGGGTGTGTTAAAT
TGAAAGCGAGAAATAATCATAAATTATTCATTATCGGGATATCCGTTAAGTTGTATCGTA

FIG. 3C [CTCGAGGGTACCCCGGG] ATG-GGA-TCC-CCG-GGT-ACC-GAG-CTC-TCG-AGT-AAA-TAA-ATA-ATTTTTAT]
Xhol Kpnl Smal BamHI Kpnl Xhol Sacl STOP term

FIG. 3D [ATG-GGG-ATC-CCC-GGG-TAC-CGA-GCT-CTC-GAG-TAA-ATA-AAT-AA-ATTTTTAT]
BamHI Kpnl Smal Xhol Sacl STOP term

FIG. 3E [ATG-GGG-GAT-CCC-CGG-GTA-CCG-AGC-TCT-CGA-GTA-AAT-AAA-TAA-ATTTTTAT]
BamHI Kpnl Smal Xhol Sacl STOP term

FIG. 3F [CTCGAGGGATCCCGGGTACCGAGCTCTAAATAAATAATTTTTAT]
Xhol BamHI Smal Kpnl Sacl STOP term

RECOMBINANT POXVIRUS HOST RANGE SELECTION SYSTEM

This invention was made with Government support under contract DAMD17-85-C-5232 awarded by the Department of the Army. The Government has certain rights in this invention.

FIELD OF THE INVENTION

The present invention relates to modified poxvirus, particularly modified vaccinia virus, and to methods of making and selecting for the same. More in particular, the invention relates to a selection system for the cloning and expression of an open reading frame in recombinant poxvirus, particularly recombinant vaccinia virus.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (32).

Specifically, the recombinant poxviruses are constructed in two steps known in the art and analogous to the methods for creating synthetic recombinants of the vaccinia virus described in U.S. Pat. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of nonessential DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a non-essential region of pox DNA. The resulting plasmid construct is then amplified by growth within E. coli bacteria (4) and isolated (5,22).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Unperturbed, successful recombination occurs at a frequency of approximately 0.1%.

A basic screening strategy for recovering those viruses modified by a successful recombination involves in situ hybridization of recombinants on replica filters with a radiolabeled probe homologous to the inserted sequences (26,28). A number of modifications have been reported to increase the efficiency of recombination itself or to facilitate the identification of recombinants. Among these modifications are included: using single stranded donor DNA (38); identification of recombinants expressing unique enzymatic functions such as $^{125}$Iododeoxycytidine incorporation into DNA via expression of the Herpes simplex virus thymidine kinase (28); chromogenic substrates for (co)expression of foreign genes along with B galactosidase (3,29); selection for thymidine kinase expression (20,28); antibody based reactions to visualize recombinant plaques (21); use of conditional lethal ts or drug mutants (9,18); selection of recombinants using the neomycin resistance gene from Tn5 and the antibiotic G418 (11); or selection pressures with mycophenolic acid and the E. coli gpt gene (2,8).

Disadvantageously, these known methods for identifying or selecting recombinant poxvirus all involve tedious multi-step identification of the recombinants, the introduction of radiochemicals, chromogenic substrates, biochemicals useful for selection such as mycophenolic acid and bromodeoxyuridine which may be detrimental (mutagenic) to the viral genome itself, use of serological reagents that may introduce contaminants, and typically the presence of an exogenous gene in the final recombinant in addition to the foreign genetic element of interest.

It can thus be appreciated that provision of a method of making and selecting for poxvirus recombinants, particularly vaccinia recombinants, which method avoids the previously discussed problems, would be a highly desirable advance over the current state of technology.

OBJECTS OF THE INVENTION

It is therefore an object of this invention to provide rapid one-step identification of recombinant viruses and rapid screening for expression of the foreign open reading frames in the recombinants.

It is a second object of this invention to provide a method of making and selecting for a recombinant poxvirus, particularly recombinant vaccinia virus, and to provide DNA sequences, produced or involved as intermediates in the method.

It is an additional object of this invention to provide a selection system for the cloning and expression of an open reading frame in recombinant poxvirus, particularly recombinant vaccinia virus, wherein the recombinant virus contains no foreign gene other than the open reading frame of interest.

These and other objects and advantages of the present invention will become more readily apparent after consideration of the following.

STATEMENT OF THE INVENTION

In one aspect, the present invention relates to a method for selecting for a recombinant poxvirus in a host by combining donor DNA and a modified poxvirus to form a recombinant poxvirus and identifying the recombinant poxvirus by its ability to replicate in the host. In another aspect, the present invention relates to a method for cloning and expressing an open reading frame in a recombinant poxvirus in a host by combining donor DNA and a modified poxvirus to form a recombinant poxvirus, replicating the recombinant poxvirus in the host and expressing the open reading frame.

According to the present invention, the modified poxvirus has a host range gene deleted therefrom so that the modified poxvirus does not replicate in the host and the donor DNA contains an open reading frame from a non-pox source and the host range gene for permitting the recombinant poxvirus to replicate in the host.

In yet another aspect, the invention relates to a donor plasmid for making the recombinant poxvirus of the selection system. The donor plasmid contains an open reading frame from a non-pox source and a host range gene for permitting the recombinant poxvirus to replicate in the host. Advantageously, the donor plasmid may also contain a promoter upstream from the poxvirus host range gene, a translation initiation codon downstream from the promoter followed by unique multiple restriction sites, translational termination signal sequences and an early transcription termination signal sequence.

BRIEF DESCRIPTION OF THE DRAWINGS

A better understanding of the present invention will be had by referring to the accompanying drawings, in which:

FIG. 1A schematically shows a method for the construction of the vaccinia virus deletion/recombinant vP293;

FIG. 1B is a map of the left end of the rescuing vaccinia virus VTK−79 through HindIII K;

FIG. 1C is a map of the left end of the vaccinia virus deletion/recombinant vP293 through HindIII K;

FIG. 2A schematically shows a method for cloning of the host range gene KlL into the plasmid pMP528L and its insertion into vP293 to generate vaccinia virus vP457;

FIG. 2B is a map of the left end of vP293 through HindIII K;

FIG. 2C is a map of the left end of vP457 through HindIII K;

FIG. 3A schematically shows a method for the construction of plasmids pMP528HRH and pHES1-4;

FIG. 3B shows the DNA sequence of the synthetic H6 promoter and downstream restriction sites present in pMP528HRH;

FIG. 3C shows the DNA sequence (with restriction sites, stop codons and early transcriptional termination signal) which replaces the bracketed sequence of FIG. 3B in plasmid pHES1;

FIG. 3D shows the DNA sequence (with restriction sites, stop codons and early transcriptional termination signal) which replaces the bracketed sequence of FIG. 3B in plasmid pHES2;

FIG. 3E shows the DNA sequence (with restriction sites, stop codons and early transcriptional termination signal) which replaces the bracketed sequence of FIG. 3B in plasmid pHES3; and FIG. 3F shows the DNA sequence (with restriction sites, stop codons and early transcriptional termination signal) which replaces the bracketed sequence of FIG. 3B in plasmid pHES4.

DETAILED DESCRIPTION OF THE INVENTION

The invention is directed to a selection system for poxvirus recombinants, particularly vaccinia recombinants, and for the cloning and expression of an open reading frame in poxvirus, particularly vaccinia virus, using a conditional lethal host range mutant of the poxvirus.

Host range mutants of rabbitpox virus (24,13) and vaccinia virus (6,7,12,17,23,36) are known.

Host range mutants of rabbitpox virus are believed to be defective in some control function required for virus replication (10). Subsequent genomic analysis of these rabbitpox virus mutants demonstrated extensive terminal deletions (up to 30 Kb) of DNA (19,25).

Nitrous acid mutagenesis of the Copenhagen strain of vaccinia virus allowed Drillien et al. (6) to isolate a host range mutant defective in replication in most human cells. Genomic analysis of this mutant revealed an extensive deletion of approximately 18 Kb toward the left terminus (6). Additional analysis by marker transfer studies mapped the genetic function responsible for host range to a 5.2 Kb EcoRI fragment (14) and finally to an 855 bp open reading frame overlapping the HindIII M/K fragments (15).

The host range gene of the WR strain of vaccinia virus (27,30) is located between 24 and 25.2 Kb from the left end of the vaccinia genome. This host range gene, transcribed leftward from HindIII K into HindIII M, is described herein as the KlL gene following the nomenclature recommended by Rosel et al. (33).

A host range gene deletion mutant of the vaccinia WR strain was generated by insertion of the neomycin resistance gene from transposon Tn5 and selection with the antibiotic G418. This deletion/recombinant, vP293, lacks approximately 21.7 Kb of DNA beginning 3.8 Kb from the left end of the genome. vP293 is capable of plaquing on primary chick embryo fibroblasts (CEF), two monkey cell lines (BSC-40 or VERO) but is defective in replication in the human cell line MRC-5.

Insertion of the host range gene, KlL, into vP293 restores the ability for growth on MRC-5 cells.

A series of plasmids were constructed which in addition to the K1L host range gene contain a vaccinia early/late promoter, H6, preferably followed by unique polylinker sequence multicloning restriction sites, translational initiation and termination codons, and an early transcription termination signal. These plasmids, pMP528HRH and pHES1-4, allow for the rapid single step, cloning and expression of any open reading frame when recombined with vP293 and scored for growth on MRC-5 cells.

Insertion of a foreign open reading frame into these plasmids followed by recombination with vP293 will simultaneously restore the host range function (KlL gene) and introduce the foreign open reading frame into the rescuing virus, vP293. The recombinant viruses are identified by their ability to plaque on MRC-5 cells.

Advantages of this system include the absence of any non-vaccinia exogenous gene in the final recombinant other than the genetic element of interest, no genetic reversion of the virus since vP293 is a deletion mutant of KlL, and the rapid one step identification of recombinants. This single step can also be used for rapid screening of expression of the foreign gene, for example, for epitope mapping.

Additional plasmids containing the KlL host range gene have been constructed where the H6 early/late promoter has been replaced with either a strictly early or a strictly late vaccinia promoter. With such additional plasmids the subtleties of temporal regulation of expression of foreign genetic elements can be studied.

A better understanding of the present invention and of its many advantages will be had from the following examples, given by way of illustration.

The WR strain of vaccinia virus was utilized in these examples. Its origin and conditions of cultivation have been previously described (27). Primary chick embryo fibroblasts (CEF), monkey cell lines (VERO [ATCC# CCL81] and BSC40), and the human cell line MRC-5 (ATCC# CCL171) were cultivated in Eagle's minimal essential medium (MEM) containing 5% (VERO and BSC40) or 10% (MRC-5, CEF) fetal bovine serum (FBS).

Plasmids were constructed, screened, and grown by standard procedures (22,31,32).

Example 1

Construction Of Plasmid pMP528PiN And Generation Of vP293

Referring to FIG. 1A, an EcoRI/SalI fragment comprising the left terminal 3.8 Kb of vaccinia DNA was isolated from pAG5 (30) and inserted into pUC13 previously cut with EcoRI and SalI. The resulting plasmid, pMP5, was digested with HindIII and SalI and ligated with a 3.8 HindIII/SalI fragment containing vaccinia sequences corresponding to the right end of the vaccinia HindIII fragment K. The resulting plasmid pMP528 thus contains the 3.8 Kb of the left terminus of the vaccinia genome and 3.8 Kb from the right end of the HindIII K fragment deleting the intervening 21.7 Kb between the SalI sites at 3.8 and 25.5 Kb from the left end of the genome. The unique SalI site in pMP528 was changed to a SmaI site by addition of synthetic linkers (commercially available from Collaborative Research, Inc., Bedford, Mass.) producing pMP528L. A 1.4 Kb SmaI fragment containing the gene for neomycin phosphotransferase from transposon Tn5 (1) was isolated from pSV2-neo (35, ATCC# 37149) and put under the control of an early vaccinia promoter (designated here as Pi).

The Pi promoter, from the AvaI H region of vaccinia, has been described (37). More in particular, this promoter is derived from the AvaI H (XhoI G) fragment of the L-variant WR vaccinia strain, in which the promoter directs transcription from right to left. The map location of the promoter is approximately 1.3 Kb from the left end of AvaI H, approximately 12.5 Kb from the left end of the vaccinia genome, and about 8.5 Kb left of the HindIII C/N junction. The promoter was located by standard transcriptional mapping analysis. The Pi DNA sequence corresponds to the region upstream from an open reading frame coding for a 5KD glycine-rich protein recently described (40). This promoter element has been shown to express foreign genes in vaccinia recombinants at early times after infection (37).

A SmaI ended Pi promoter/neo gene cassette was ligated into the SmaI site of pMP528L producing pMP528PiN. pMP528PiN contains 0.4 Kb of vaccinia sequences derived from a Sau3A subclone of AvaI H containing the Pi promoter region followed by 1 Kb of Tn5 sequences from the BglII through SmaI sites (1).

pMP528PiN was transfected into primary CEF and coinfected with the rescuing vaccinia virus, VTK−79, by standard procedures (28). Recombinant virus was selected and grown on primary CEF in the presence of 300 ug/ml G418 (1,11,35).

The genomic configurations of recombinant vaccinia vP293 were confirmed by Southern blot hybridization analysis. The recombinant vaccinia vP293 had been deleted of 21.7 Kb of vaccinia as predicted and contained the foreign gene encoding neo$^r$. The restriction map of the left terminus of the rescuing virus VTK−79 and of the recombinant virus vP293 expressing the neo$^r$ gene and selected on primary CEF in the presence of G418 are indicated in FIGS. 1B and 1C.

In the absence of the antibiotic G418, vP293 produced large plaques on primary CEF and plaqued well on BSC40 or VERO cells although vP293 plaques were detectably smaller than the parent VTK−79 on VERO cells. Significantly, vP293 gave no measurable replication and failed to form plaques on the human cell line MRC-5.

Example 2

Reconstruction Of vP293 With The Host Range Gene, KlL

To demonstrate that the host range gene, KlL, when reconstituted into the deletion mutant vP293 of the WR strain of vaccinia would allow the virus to replicate on human cells, the host range gene, KlL, was cloned into the plasmid pMP528L and inserted into vP293.

Referring now to FIG. 2A, the vaccinia DNA sequence composing the right arm of pMP528L (FIGS. 1A and 2A) was shortened to eliminate unwanted restriction sites and to facilitate future cloning steps. pMP528L was cut by EcoRV/HindIII, blunt ended with the Klenow fragment of the *E. coli* polymerase and self ligated. In this manner, the right arm of the resulting plasmid pMP528E was reduced in length to 0.4 Kb of DNA.

An 891 bp vaccinia BglII (partial)/HpaI fragment containing the entire coding sequence and promoter from the KlL host range gene (15) was prepared from pSD452VC, a subclone of Copenhagen strain vaccinia containing sequences from HindIII M and K. The K1L containing fragment was cloned into the polylinker region of pUC8 for the sole purpose of flanking the gene with convenient restriction sites. The resulting plasmid pUC8HR was digested with HindIII and SmaI to isolate the K1L containing fragment. The HindIII end was filled in with the Klenow fragment of the E. coli DNA polymerase and the fragment cloned in the SmaI site of pMP528E. A plasmid pMP528HR with the orientation of the K1L host range gene reading leftward as shown in FIG. 2A was isolated by standard procedures.

Procedures for recombination and hybridization on nitrocellulose filters were as known in the art and as previously described (28) with the following modifications.

The donor plasmid pMP528HR was introduced by electroporation into either VERO or MRC-5 cells each coinfected with vP293. Subconfluent monolayers of VERO or MRC-5 cells were infected with rescuing virus for 1 hour. The cells were harvested with trypsin, washed with Hepes buffered saline (HeBS) (16), and electroporated in the presence of 25 ug of plasmid DNA in HeBS. Virus-infected cells were electroporated using a Bio-Rad Gene Pulser equipped with a Bio-Rad Gene Pulser Capacitance Extender. The cell suspension (0.8 ml) was placed on ice for 10 minutes in a Bio-Rad gene pulser cuvette, then pulsed at 200 volts (capacitance 960 uFD) and placed on ice for another 10 minutes. The cells were then diluted in 8 ml MEM + 5% FBS, plated in 60 mm dishes containing corresponding VERO or MRC-5 cell monolayers (4 ml per dish), and incubated at 37° C. overnight.

Progeny was harvested and plated on either VERO or MRC-5 cells. The number of plaques obtained on VERO cells was 10 to 100 times greater than the number of plaques obtained on MRC-5 cells. Isolated plaques (of uniform size) were picked from MRC-5 and from VERO cell cultures (both large and small sized plaques). These plaque isolates were replated on VERO cells and after three days the resulting plaques were lifted onto nitrocellulose filter disks and prepared for in situ hybridization (26). All the plaques originating from MRC-5 cells and all the larger plaques but not the smaller sized plaques derived from VERO cells gave positive hybridization signals when probed with a $^{32}P$ labeled probe to the K1L coding sequences. This data is consistent with restoration of host range functions contained in the K1L coding sequence.

An isolate obtained from MRC-5 cells was further purified and designated vP457. In vP457 the K1L gene had been restored and was situated within the deletion in its native orientation reading from right to left. The KlL sequences had replaced the Pi promoter/neomycin phosphotransferase gene cassette present in vP293 as shown in FIGS. 2B and 2C. Compared to the genome of the L variant vaccinia (30,27) vP457 contains a 291 bp deletion to the right of the KlL gene and a 20.2 Kb deletion to the left of the KlL gene.

Example 3

Construction Of Plasmids pMP528HRH And pHES1–4.

To demonstrate that the conditional lethal mutation in vP293 could be exploited for constructing donor plasmids into which additional open reading frames could be cloned, a series of plasmids, pMP528HRH and pHES1–4, were constructed. Recombination of exogenous open reading frames present in a plasmid containing the KlL host range gene into vP293 would yield a simple method for generating vaccinia recombinants by virtue of host range restriction.

A vaccinia promoter, H6, was added upstream from the KlL gene in pMP528HR. This early/late promoter was previously identified by standard transcriptional mapping and DNA sequence analysis. It has the sequence (positions −125 to +3) ATTCTTTATT-CTATACTTAAAAAAT-GAAAATAAATACAAAGGTTCTT-GAGGGTTGTGTTAA ATTGAAAGC-GAGAAATAATCATAAATTATTTCATTATCG-CGATATCCGTTAAGTTTGTATC GTAATG. The sequence is that described as being upstream of open reading frame H6 by Rosel et al. (33).

Referring now to FIG. 3, DNA corresponding to positions −124 to −1 (with position −102 changed from A to G in order to prevent the introduction of any potential initiation codons) and followed by XhoI, KpnI, and SmaI restriction sites was synthesized chemically (FIG. 3B) and cloned into the SmaI site of pMP528HR producing pMP528HRH (FIG. 3A). Thus, pMP528HRH contains the H6 promoter upstream from the KlL gene which is expressed under the control of the KlL endogenous promoter. Both are in a right to left orientation with respect to vaccinia arms (genome). The H6 promoter in pMP528HRH is immediately upstream of unique XhoI, KpnI, and SmaI restriction sites.

To increase further the utility of the system a series of plasmids pHES1–4 were derived from pMP528HRH. pHES1 was constructed by the following procedure: pMP525HRH was cut with XhoI and XmaI, and the oligonucleotides HRL1 5′ (TCGACCATGGGATCCCCGGGTACC-GAGCTCTCGAGTAAATAAATAATTTT-TAT)3′ and HRL2 5′ (CCGGATAAAAATTATTTATTTACT-CGAGAGCTCGGTACCCGGGGATC-CCATGG)3′ cloned into this site. pHES2, pHES3 and pHES4 were similarly constructed. pHES2 was constructed with the oligonucleotides HRL3 5′ (TCGACCATGGGGATCCCCGGGTACC-GAGCTCTCGAGTAAATAAATAATTTT-TAT)3′ and HRL4 5′ (CCGGATAAAAATTATTTATTTACT-CGAGAGCTCGGTACCCGGGGATCC-CCATGG)3′, pHES3 was constructed with the oligonucleotides HRL5 5′ (TCGACCATGGGGGATCCCCGGGTACC-GAGCTCTCGAGTAAATAAATAATTTT-TAT)3′ and HRL6 5′ (CCGGATAAAAATTATTTATTTACT-CGAGAGCTCGGTACCCGGGGATCCC-CCATGG)3′ and pHES4 was constructed with the oligonucleotides HRL7 5′ (TCGAGGATCCCGGGTACCGAGCT-CTAAATAAATAATTTTTAT)3′ and HRL8 5′ (CCGGATAAAAATTATTTATT-TAGAGCTCGGTACCCGGGATCC)3′.

The pertinent DNA sequence elements, restriction sites, and transcriptional and translational signals of pMP528HRH and pHES1–4 are as follows.

The sequence of the synthetic H6 promoter (positions −124 through −1, with the altered base at position −102 underlined) and downstream restriction sites present in pMP528HRH are shown in FIG. 3B.

The bracketed sequence is replaced in plasmids pHES1–4, with restriction sites, stop codons, and early transcriptional termination signal as indicated, as shown in FIG. 3C for pHES1, in FIG. 3D for pHES2, in FIG. 3E for pHES3, and in FIG. 3F for pHES4.

In addition to the elements contained in pMP528HRH, each plasmid, pHES1–3, contains a translation initiation codon downstream from the H6 promoter followed by unique multiple restriction sites, translational termination signal sequences, and a specific vaccinia early transcription termination signal sequence (39). Each plasmid, pHES1–3, contains a translation initiation codon in one of the three reading frames. Therefore any DNA sequence which contains an open reading frame can be expressed when cloned into one of these plasmids and recombined into vaccinia virus.

The fourth plasmid, pHES4, does not contain a translation initiation codon but does contain unique multiple restriction sites, translational termination sequences, and an early transcription termination signal sequence.

D-galactopyranocide, Boehringer Mannheim) and blue color development scored after 8 hours.

When progeny was plated on VERO cells and expression of B galactosidase assayed in the presence of X-gal no blue plaques were observed in cells transfected with pHESLZ1, 2 or 4. Significantly, approximately 20% of the plaques generated with plasmid pHESLZ3 gave blue plaques in the presence of X-gal (data not shown).

When progeny was plated on VERO cells and recombinant viruses screened by in situ hybridization, 12 to 22% of the plaques gave positive hybridization signals to lacZ (Table 1A). When analyzed by in situ DNA hybridization (26) every plaque on MRC-5 demonstrated the presence of the lacZ gene (Table 1B). B galactosidase activity, however, was seen only in those plaques on MRC-5 which were derived from pHESLZ3 (Table 1C). Only the plasmid construct pHESLZ3 had the lacZ gene in frame with the translational initiation codon.

TABLE 1

Analysis of recombinant lacZ/vaccinia virus generated with plasmids pHESLZ1-4 and vP293 vaccinia virus

| | | Donor Plasmid | | |
|---|---|---|---|---|
| | pHESLZ1 | pHESLZ2 | pHESLZ3 | pHESLZ4 |
| A. Total Plaques Hybridization | 1056 | 637 | 793 | 1344 |
| Positive | 153 | 141 | 95 | 269 |
| Percent Positive | 14.5 | 22 | 12 | 20 |
| B. Total Plaques Hybridization | 60 | 56 | ND | 71 |
| Positive | 60 | 56 | ND | 71 |
| Percent Positive | 100 | 100 | | 100 |
| C. Total Plaques | 60 | 55 | 59 | 70 |
| X-gal Positive | 0 | 0 | 59 | 0 |
| Percent Positive | 0 | 0 | 100 | 0 |

A DNA sequence which contains an open reading frame and an initiation codon can be expressed when cloned into pHES4 and recombined into vaccinia virus.

Example 4

Incorporation Of The Bacterial LacZ Gene Into Vaccinia Virus And Selection Of The Recombinant Viruses On The Basis Of Host Range Restriction.

To demonstrate the utility of the pHES1–4/vP293 host range selection system, a recombinant vaccinia virus containing the E. coli lacZ gene encoding B galactosidase was constructed.

A BamHI fragment containing codons 8 through the end of the lacZ gene was obtained from pMC1871 (34). This lacZ BamHI fragment was cloned into the unique BamHI site of the plasmids pHES1–4.

Recombination between the resulting plasmids pHESLZ1–4 transfected individually into VERO cells coinfected with the host range mutant vP293 was performed.

After 24 hours post infection, progeny virus was harvested by three freeze/thaw cycles and plated on either VERO (Table 1A) or MRC-5 (Table 1B and 1C) cells.

VERO and MRC-5 monolayers (Table 1A and 1B), stained with neutral red, were lifted after 3 days onto nitrocellulose filters and prepared for in situ hybridization (26) using a $^{32}P$ labeled lacZ gene probe. VERO (data not shown) and MRC-5 monolayers (Table 1C) were exposed to X-gal (5-bromo-4-chloro3-indolyl-B-

REFERENCES

1. Beck, E., Ludwig, G., Auerswald, E.A., Reiss, B., and H. Schaller, Gene 19, 327–336 (1982).
2. Boyle, D.B. and B.E.H. Coupar, Gene 65, 123–128 (1988).
3. Chakrabarti, S., Brechling, K., and B. Moss, Mol. Cell. Biol. 5, 3403–3409 (1985).
4. Clewell, D.B., J. Bacteriol. 110, 667–676 (1972).
5. Clewell, D.B. and D.R. Helinski, Proc. Natl. Acad. Sci. USA 62, 1159–1166 (1969).
6. Drillien, R., Koehren, F., and A. Kirn, Virology 111, 88–499 (1981).
7. Drillien, R., Spehner, D., and A. Kirn, J. Virol. 28, 843–850 (1978).
8. Falkner, F.G. and B. Moss, J. Virol. 62, 1849–1854 (1988).
9. Fathi, Z., Sridhar, P., Pacha, R.F., and R.C. Condit, Virology 155, 97–105 (1986).
10. Fenner, F., and J.F. Sambrook, Virology 28, 600–609 (1966).
11. Franke, C.A., Rice, C.M., Strauss, J.H., and D.E. Hruby, Mol. Cell. Biol. 5, 1918–1924 (1985).
12. Gangemi, J.D., and D.G. Sharp, Virology 85, 262–270 (1978).
13. Gemmell, A., and F. Fenner, Virology 11, 219–235 (1960).
14. Gillard, S., Spehner, D., and R. Drillien, J. Virol. 53, 316–318 (1985).
15. Gillard, S., Spehner, D., Drillien, R., and A. Kirn, Proc. Natl. Acad. Sci. USA 83, 5573–5577 (1986).

16. Graham, F.L. and A.J. Van der Eb, Virology 54, 536-539 (1973).
17. Hruby, D.E., Lynn, D.L., Condit, R., and J.R. Kates, J. Gen. Virol. 47, 485-488 (1980).
18. Kieny, M.P., Lathe, R., Drillien, R., Spehner, D., Skory, S., Schmitt, D., Wictor, T., Koprowski, H., and J.P. lecocq, Nature(london) 312 163-166 (1984)
19. Lake, J.R., and P.D. Cooper, J. Gen. Virol. 48, 135-147 (1980).
20. Mackett, M., Smith, G.L. and B. Moss, Proc. Natl. Acad. Sci. USA 79, 7415-7419 (1982).
21. Mackett, M. and J.R. Arrand, EMBO J. 4, 3229-3235 (1985).
22. Maniatis, T., Fritsch, E.F., and J. Sambrook, Molecular Cloning: A Laboratory Manual, (Cold Spring Harbor Laboratory, New York) (1982).
23. Mayr, A., Hochstein-Mintzel, V., and H. Stickl, Infection 3, 6-14 (1975).
24. McClain, M.E., Aust. J. exp. Biol. med. Sci. 43, 31-44 (1965).
25. Moyer, R.W. and C.T. Rothe, Virology 102, 119-132 (1980).
26. Nakano, E., Panicali, D., and E. Paoletti, Proc. Natl. Acad. Sci. USA 79, 1593-1596 (1982).
27. Panicali, D., Davis, S.W., Mercer, S.R. and E. Paoletti, J. Virol. 37, 1000-1010 (1981).
28. Panicali, D., and E. Paoletti, Proc. Natl. Acad. Sci. USA 79, 4927-4931 (1982).
29. Panicali, D., Grzelecki, A., and C. Hwang, Gene 47, 193-199 (1986).
30. Perkus, M.E. Panicali, D., Mercer, S., and E. Paoletti, Virol. 152, 285-297 (1986).
31. Perkus, M.E., Piccini, A., Lipinskas, B.R., and E. Paoletti, Science 229, 981-984 (1985).
32. Piccini, A., Perkus, M.E. and E. Paoletti, In: Methods in Enzymology, Vol. 153, ed. Wu, R. and L. Grossman (Academic Press), pp. 545-563 (1987).
33. Rosel, J.L., Earl, P.L., Weir, J.P., and B. Moss, J. Virol. 60 436-449 (1986).
34. Shapira, S.K., Chou, J., Richaud, F.V., and M.J. Casadaban, Gene 25, 71-82 (1983).
35. Southern, P.H. and P. Berg, J. Mol. Appl. Genet. 1, 327-341 (1982).
36. Tagaya, I., Kitamura, T., and Y. Sano, Nature (London) 192, 381-382 (1961).
37. Wachsman, M., Aurelian, L., Smith, C.C., Lipinskas, B.R., Perkus, M.E., and E. Paoletti, J. Inf. Dis. 155, 1188-1197 (1987).
38. Wilson, E.M., W.M. Hodges and D.E. Hruby, Gene 49, 207-213 (1986).
39. Yuen, L., and B. Moss, Proc. Natl. Acad. Sci. USA 84, 6417-6421 (1987).
40. Kotwal, G. J. and B. Moss, Virology 167, 524-537 (1988).

I claim:

1. A method for selecting for a recombinant vaccinia virus in a host, which method comprises combining by recombination donor DNA in a plasmid and a modified vaccinia virus by co-transformation, transfection or infection of the plasmid and virus in a cell to form a recombinant vaccinia virus, said modified vaccinia virus having a host range gene detect therefrom so that the modified vaccinia virus does not replicate in the host, and said donor DNA comprising (a) an open reading frame from a non-vaccinia source, and (b) the host range gene for permitting the recombinant vaccinia virus to replicate in the host, (c) flanking DNA which is homologous to the modified vaccinia virus so as to achieve recombination, and (d) a promoter sequence to control expression of the open reading from; and identifying the recombinant vaccinia virus by its ability to replicate in the host.

2. A method as claimed in claim 1, wherein the open reading frame from the non-vaccinia source is an *E. coli* lacZ gene encoding B galactosidase.

3. A method as claimed in claim 1, wherein the host is a human cell line.

4. A method as claimed in claim 3, wherein the human cell line is MRC-5.

5. A method as claimed in claim 1, wherein the host range gene is vaccinia host range gene KIL.

6. A method for cloning and expressing an open reading frame in a recombinant vaccinia virus in a host, which method comprises:

combining by recombination donor DNA in a plasmid and a modified vaccinina virus by co-transformation, transfection or infection of the plasmid and virus in a cell to form a recombinant vaccinia virus, said modified vaccinia virus having a host range gene deleted therefrom so that the modified vaccinia virus does not replicate in the host, and said donor DNA comprising (a) an open reading frame from a non-vaccinia source, (b) the host range gene for permitting the recombinant vaccinia virus to replicate in the host, (c) flanking DNA which is homologous to the modified vaccinia virus so as to achieve recombination, and (d) a promoter sequence to control expression of the open reading frame;

replicating the recombinant vaccinia virus in the host; and expressing the open reading frame.

7. A method as claimed in claim 6, wherein the open reading frame from the non-vaccinia source is an *E. coli* lacZ gene encoding B galactosidase.

8. A method as claimed in claim 6, wherein the host is a human cell line.

9. A method as claimed in claim 8, wherein the human cell line is MRC-5.

10. A method as claimed in claim 6, wherein the host range gene is vaccinia host range gene KIL.

* * * * *

UNITED STATES PATENT AND TRADEMARK OFFICE
CERTIFICATE OF CORRECTION

PATENT NO. : 5,155,020

DATED : October 13, 1992

INVENTOR(S) : Enzo Paoletti

It is certified that error appears in the above-identified patent and that said Letters Patent is hereby corrected as shown below:

Claim 1, line 8, column 12, line 6, change "detect" to --deleted--;

line 17, column 12, line 15, change "from" to --frame--.

Claim 6, line 5, column 12, line 31, correct the spelling of "vaccinia".

Signed and Sealed this

Twenty-first Day of September, 1993

*Attest:*

BRUCE LEHMAN

*Attesting Officer*     Commissioner of Patents and Trademarks